US012275934B2

(12) United States Patent
Zhai et al.

(10) Patent No.: US 12,275,934 B2
(45) Date of Patent: Apr. 15, 2025

(54) **STRAIN OF *LACTOBACILLUS RHAMNOSUS* AND APPLICATION THEREOF IN INHIBITING *HELICOBACTER PYLORI***

(71) Applicant: Jiangnan University, Wuxi (CN)

(72) Inventors: Qixiao Zhai, Wuxi (CN); Wei Chen, Wuxi (CN); Jianxin Zhao, Wuxi (CN); Meiyi Zhang, Wuxi (CN); Shumao Cui, Wuxi (CN); Wenwei Lu, Wuxi (CN); Fengwei Tian, Wuxi (CN); Leilei Yu, Wuxi (CN); Gang Wang, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 456 days.

(21) Appl. No.: 17/711,257

(22) Filed: Apr. 1, 2022

(65) Prior Publication Data

US 2022/0228106 A1    Jul. 21, 2022

Related U.S. Application Data

(63) Continuation of application No. PCT/CN2021/095678, filed on May 25, 2021.

(30) Foreign Application Priority Data

May 29, 2020 (CN) .......................... 202010478076.0

(51) Int. Cl.
*C12N 1/20* (2006.01)
*A23L 33/00* (2016.01)
*A23L 33/135* (2016.01)
*A61K 35/747* (2015.01)
*A61P 31/04* (2006.01)
*C12R 1/225* (2006.01)

(52) U.S. Cl.
CPC ............ *C12N 1/205* (2021.05); *A23L 33/135* (2016.08); *A23L 33/40* (2016.08); *A61K 35/747* (2013.01); *A61P 31/04* (2018.01); *A23V 2002/00* (2013.01); *A23V 2400/175* (2023.08); *C12R 2001/225* (2021.05)

(58) Field of Classification Search
CPC ..... C12N 1/205; A23L 333/135; A23L 33/40; A61P 31/04; A61K 35/747; C12R 2001/225; A23V 2400/175; A23V 2002/00
See application file for complete search history.

(56) References Cited

PUBLICATIONS

Ellis (Vaccines, W.B. Saunders Company, Chapter 29, 1988, pp. 568-574).*
Boslego et al (Vaccines and Immunotherapy, 1991, Chapter 17).*

* cited by examiner

*Primary Examiner* — Robert A Zeman
(74) *Attorney, Agent, or Firm* — IPRO, PLLC

(57) ABSTRACT

The disclosure discloses a strain of *Lactobacillus rhamnosus* and application thereof in inhibiting *Helicobacter pylori*, and belongs to the technical fields of microorganisms and medicine. The disclosure provides a strain of *Lactobacillus rhamnosus* CCFM1119. The *Lactobacillus rhamnosus* CCFM1119 can prevent and/or treat *Helicobacter pylori* infection, specifically embodied in that: (1) the *Lactobacillus rhamnosus* CCFM1119 can significantly relieve the gastrointestinal symptoms of patients with *Helicobacter pylori* infection; (2) the *Lactobacillus rhamnosus* CCFM1119 can significantly reduce the amount of colonization of *Helicobacter pylori* in patients with *Helicobacter pylori* infection; and (3) the *Lactobacillus rhamnosus* CCFM1119 can significantly increase the clearance rate of *Helicobacter pylori* in patients with *Helicobacter pylori* infection. Therefore, *Lactobacillus rhamnosus* CCFM1119 has great application prospects in the preparation of products (such as food or medicine) for preventing and/or treating *Helicobacter pylori* infection.

5 Claims, 2 Drawing Sheets

Specification includes a Sequence Listing.

SEQUENCE LISTING

```
<160> NUMBER OF SEQ ID NOS: 1

<210> SEQ ID NO 1
<211> LENGTH: 852
<212> TYPE: DNA
<213> ORGANISM: Lactobacillus rhamnosus

<400> SEQUENCE: 1
ctatacatgc agtcgaacga gttctgatta ttgaaaggtg cttgcatctt gatttaattt     60
tgaacgagtg gcggacgggt gagtaacacg tgggtaacct gcccttaagt ggggggataac    120 atttggaaac agatgctaat accgcataaa tccaagaacc gcatggttct tggctgaaag    180
atggcgtaag ctatcgcttt tggatggacc cgcggcgtat tagctagttg gtgaggtaac    240
ggctcaccaa ggcaatgata cgtagccgaa ctgagaggtt gatcggccac attgggactg    300
agacacggcc caaactccta cgggaggcag cagtagggaa tcttccacaa tggacgcaag    360
tctgatggag caacgccgcg tgagtgaaga aggctttcgg gtcgtaaaac tctgttgttg    420
gagaagaatg gtcggcagag taactgttgt cggcgtgacg gtatccaacc agaaagccac    480
ggctaactac gtgccagcag ccgcggtaat acgtaggtgg caagcgttat ccggatttat    540
tgggcgtaaa gcgagcgcag gcggtttttt aagtctgatg tgaaagccct cggcttaacc    600
gaggaagtgc atcggaaact gggaaacttg agtgcagaag aggacagtgg aactccatgt    660
gtagcggtga aatgcgtaga tatatggaag aacaccagtg gcgaaggcgg ctgtctggtc    720
tgtaactgac gctgaggctc gaaagcatgg gtagcgaaca ggattagata ccctggtagt    780
ccatgccgta aacgatgaat gctaggtgtt ggagggtttc cgcccttcag tgccgcagct    840
aacgcattaa gc                                                          852
```

STRAIN OF *LACTOBACILLUS RHAMNOSUS* AND APPLICATION THEREOF IN INHIBITING *HELICOBACTER PYLORI*

TECHNICAL FIELD

The disclosure relates to a strain of *Lactobacillus rhamnosus* and application thereof in inhibiting *Helicobacter pylori*, and belongs to the technical fields of microorganisms and medicine.

BACKGROUND

*Helicobacter pylori* (Hp) is a microaerophilic gram-negative bacterium that colonizes the surface of the gastric mucosa and the duodenum. *Helicobacter pylori* was first discovered by Marshall and Warren, and the two scholars won the 2005 Nobel Prize in Physiology or Medicine. *Helicobacter pylori* is one of the main epidemic pathogens, and its detection rate in the global population has exceeded 50%. The low level of economic development and poor sanitary conditions are the two main factors for the prevalence of *Helicobacter pylori* infection. In developed countries, the infection rate of *Helicobacter pylori* in adults is about 30-40%, and in developing countries, the infection rate of *Helicobacter pylori* in adults is as high as about 80-90%.

After infection, *Helicobacter pylori* is generally difficult to clear spontaneously, leading to lifelong infections. *Helicobacter pylori* will disappear automatically unless eradication treatment is performed, or severe intestinal metaplasia occurs in the gastric mucosa and makes it difficult for bacteria to colonize. Studies have shown that long-term infection of *Helicobacter pylori* can cause chronic gastritis and duodenal ulcer, and eventually develop into gastric cancer. Gastrointestinal Symptom Rating Scale (GSRS) is an important indicator for evaluating gastric health symptoms, including 15 symptoms such as abdominal pain, acid reflux, nausea and vomiting, borborygmus, belching, increased defecation, and incomplete defecation. Clinical studies have shown that *Helicobacter pylori* infection is often accompanied by a variety of gastrointestinal symptoms such as belching, nausea, abdominal distension and abdominal discomfort after a meal. These gastrointestinal symptoms greatly affect the patient's quality of life. Therefore, restoring the changes in gastrointestinal symptoms caused by *Helicobacter pylori* infection is of great significance for improving the daily life of patients.

At present, triple or quadruple therapies combined with antibiotics are mainly adopted to remove *Helicobacter pylori* in patients to restore the gastrointestinal symptoms caused by *Helicobacter pylori* infection. However, due to frequent use of antibiotics in the above treatment methods, the drug resistance of *Helicobacter pylori* is likely to increase. In addition, in the process of treating patients with the above treatment methods, patients often have serious adverse reactions (such as abdominal pain, nausea, and diarrhea), resulting in a decrease in the effective rate of treatment, and the treatment effect is often not as good as expected.

Therefore, there is still a need for a drug or treatment that will not increase the drug resistance of *Helicobacter pylori*, and at the same time, will not cause adverse reactions in patients during the treatment process, so as to improve the clinical treatment effect of *Helicobacter pylori*.

SUMMARY

Technical Problem

The technical problem to be solved by the disclosure is to provide a strain of *Lactobacillus rhamnosus* capable of inhibiting *Helicobacter pylori*.

Technical Solution

To solve the above problems, the disclosure provides a strain of *Lactobacillus rhamnosus* CCFM1119. The *Lactobacillus rhamnosus* CCFM1119 is preserved in the Guangdong Microbial Culture Collection Center, the preservation number is GDMCC NO: 61013, and the preservation date is May 6, 2020.

The *Lactobacillus rhamnosus* CCFM1119 is derived from fresh feces samples from healthy humans from Kunshan, Jiangsu. The strain was sequenced and analyzed, and the 16S rDNA sequence of the strain is shown in SEQ ID NO. 1. The sequence obtained by sequencing was compared with nucleotide sequences in GeneBank. The result shows that the strain is *Lactobacillus rhamnosus*, named *Lactobacillus rhamnosus* CCFM1119.

The colony of the *Lactobacillus rhamnosus* CCFM1119 on an MRS solid medium is milky white semi-circular convex, smooth and moist in surface, and neat in edges.

The disclosure also provides application of the above *Lactobacillus rhamnosus* CCFM1119 in inhibiting *Helicobacter pylori* not for the purposes of disease diagnosis and treatment.

The disclosure further provides a *Helicobacter pylori* inhibitor, containing the above *Lactobacillus rhamnosus* CCFM1119.

The disclosure further provides application of the above *Lactobacillus rhamnosus* CCFM1119 in the preparation of a product for preventing and/or treating *Helicobacter pylori* infection.

In one example of the disclosure, in the product, a live count of the above *Lactobacillus rhamnosus* CCFM1119 is not less than $5 \times 10^9$ CFU/mL or $5 \times 10^9$ CFU/g.

In one example of the disclosure, the product includes food or medicine.

In one example of the disclosure, the medicine contains the above *Lactobacillus rhamnosus* CCFM1119, a drug carrier and/or a pharmaceutical excipient.

In one example of the disclosure, the drug carrier includes microcapsules, microspheres, nanoparticles and/or liposomes.

In one example of the disclosure, the pharmaceutical excipient includes excipients and/or additives.

In one example of the disclosure, the excipients include binders, fillers, disintegrants and/or lubricants.

In one example of the disclosure, the additives include solubilizers, co-solvents, latent solvents and/or preservatives.

In one example of the disclosure, a preparation of the medicine is powders, granules, capsules, tablets, pills or oral liquids.

In one example of the disclosure, the food is a health food; or the food is a dairy product, a bean product, or a fruit and vegetable product produced using a starter containing the above *Lactobacillus rhamnosus* CCFM1119; or the food is a beverage or a snack food containing the above *Lactobacillus rhamnosus* CCFM1119.

In one example of the disclosure, the preparation method of the starter is: inoculating the above-mentioned *Lactoba-* cillus rhamnosus CCFM1119 into the culture medium, and the inoculation amount of the Lactobacillus rhamnosus CCFM1119 is: 2-4% of the total mass of the culture medium is inoculated, and culturing the bacteria at 37° C. for 18 h to obtain a culture solution; centrifuging the culture solution to obtain bacterial cells; washing the bacterial cells with physiological saline for 3 times and resuspending the bacterial cells with a freeze-drying protectant to obtain a resuspension; and freeze-drying the resuspension by vacuum freezing to obtain the starter.

In one example of the disclosure, a mass ratio of the freeze-drying protectant to the bacterial cells is 2:1.

In one example of the disclosure, the freeze-drying protectant contains 130 g/L skimmed milk powder.

In one example of the disclosure, the medium contains the following components (calculated as a percentage of the total mass of the medium): 87.7% water, 10% skim milk, 0.5% glucose, 1.5% tryptone, 0.3% yeast extract.

In one example of the disclosure, a pH value of the medium is 6.8.

The disclosure further provides a product for preventing and/or treating Helicobacter pylori infection, the product containing the Lactobacillus rhamnosus CCFM1119.

In one example of the disclosure, in the product, a live count of the above Lactobacillus rhamnosus CCFM1119 is not less than $5 \times 10^9$ CFU/mL or $5 \times 10^9$ CFU/g.

In one example of the disclosure, the product includes food or medicine.

In one example of the disclosure, the medicine contains the above Lactobacillus rhamnosus CCFM1119, a drug carrier and/or a pharmaceutical excipient.

In one example of the disclosure, the drug carrier includes microcapsules, microspheres, nanoparticles and/or liposomes.

In one example of the disclosure, the pharmaceutical excipient includes excipients and/or additives.

In one example of the disclosure, the excipients include binders, fillers, disintegrants and/or lubricants.

In one example of the disclosure, the additives include solubilizers, co-solvents, latent solvents and/or preservatives.

In one example of the disclosure, a preparation of the medicine is powders, granules, capsules, tablets, pills or oral liquids.

In one example of the disclosure, the food is a health food; or the food is a dairy product, a bean product, or a fruit and vegetable product produced using a starter containing the above Lactobacillus rhamnosus CCFM1119; or the food is a beverage or a snack food containing the above Lactobacillus rhamnosus CCFM1119.

In one example of the disclosure, the preparation method of the starter is: inoculate the above-mentioned Lactobacillus rhamnosus CCFM1119 into the culture medium, and the inoculation amount of the Lactobacillus rhamnosus CCFM1119 is: 2-4% of the total mass of the culture medium is inoculated, and culturing the bacteria at 37° C. for 18 h to obtain a culture solution; centrifuging the culture solution to obtain bacterial cells; washing the bacterial cells with physiological saline 3 times and resuspending the bacterial cells with a freeze-drying protectant to obtain a resuspension; and freeze-drying the resuspension by vacuum freezing to obtain the starter.

In one example of the disclosure, a mass ratio of the freeze-drying protectant to the bacterial cells is 2:1.

In one example of the disclosure, the freeze-drying protectant contains 130 g/L skimmed milk powder.

In one example of the disclosure, the medium contains the following components (calculated as a percentage of the total mass of the medium): 87.7% water, 10% skim milk, 0.5% glucose, 1.5% tryptone, 0.3% yeast extract.

In one example of the disclosure, a pH value of the medium is 6.8.

Beneficial Effects

1. The disclosure provides a strain of Lactobacillus rhamnosus CCFM1119. The Lactobacillus rhamnosus CCFM1119 can inhibit Helicobacter pylori, specifically embodied in that:
    (1) the diameter of an inhibition zone of supernatant of the Lactobacillus rhamnosus CCFM1119 on Helicobacter pylori can reach 12.92 mm; and
    (2) the Lactobacillus rhamnosus CCFM1119 can significantly reduce the adhesion of Helicobacter pylori to AGS cells.

Therefore, the Lactobacillus rhamnosus CCFM1119 has great application prospects in inhibiting Helicobacter pylori (not for the purposes of disease diagnosis and treatment) and preparing Helicobacter pylori inhibitors.

2. The disclosure provides a strain of Lactobacillus rhamnosus CCFM1119, and the Lactobacillus rhamnosus CCFM1119 can prevent and/or treat Helicobacter pylori infection, specifically embodied in that:
    (1) the Lactobacillus rhamnosus CCFM1119 can significantly relieve the gastrointestinal symptoms of patients with Helicobacter pylori infection;
    (2) the Lactobacillus rhamnosus CCFM1119 can significantly reduce the amount of colonization of Helicobacter pylori in patients with Helicobacter pylori infection; and
    (3) the Lactobacillus rhamnosus CCFM1119 can significantly increase the clearance rate of Helicobacter pylori in patients with Helicobacter pylori infection.

Therefore, Lactobacillus rhamnosus CCFM1119 has great application prospects in the preparation of products (such as food or medicine) for preventing and/or treating Helicobacter pylori infection.

3. Lactobacillus rhamnosus is a kind of probiotics, and has been included in the "List of Bacteria that Can Be Used in Food" issued by the Ministry of Health of China. Therefore, the product of the disclosure with the Lactobacillus rhamnosus CCFM1119 as an active ingredient cannot cause Helicobacter pylori to develop drug resistance, and at the same time, cannot cause adverse reactions in patients during the treatment process.

Preservation of Biological Material

A strain of Lactobacillus rhamnosus CCFM1119, taxonomically named Lactobacillus rhamnosus, was preserved at the Guangdong Microbial Culture Collection Center on May 6, 2020, the preservation number is GDMCC NO. 61013, and the preservation address is $5^{th}$ Floor, Building 59, Grand Courtyard 100, Xianlie Middle Road, Guangzhou.

DETAILED DESCRIPTION

Figure 1:
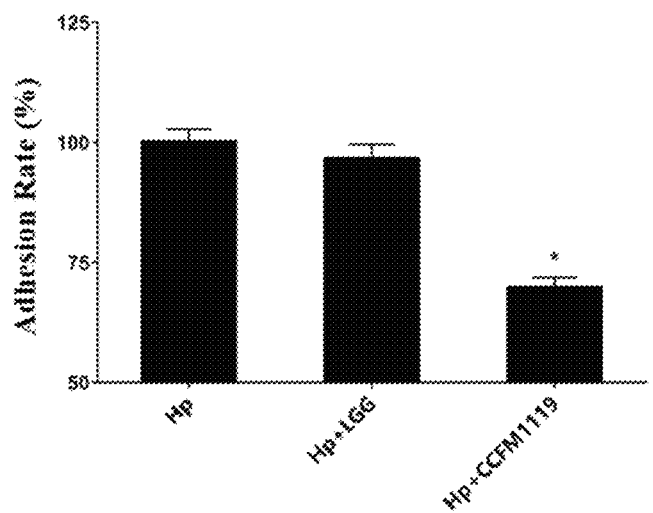
FIG. 1 shows the adhesion rate of Helicobacter pylori to AGS cells in different groups.

The *Helicobacter pylori* involved in the following examples is *Helicobacter pylori* SS1 from the National Type Culture Collection (NTCC). The *Lactobacillus rhamnosus* L. GG involved in the following examples is derived from the American Type Culture Collection (ATCC), and the preservation number is ATCC 53103. The F12 liquid medium and fetal calf serum involved in the following examples were purchased from Gibco, USA. The NaCl involved in the following examples was purchased from Sinopharm. The phenol red and urea involved in the following examples were purchased from Macklin. The Columbia medium involved in the following examples was purchased from OXOID, the United Kingdom. The sterile defibered sheep blood involved in the following examples was purchased from Hangzhou Sinry Bio-engineering Co., Ltd. The BHI liquid medium involved in the following examples was purchased from Qingdao Hope Bio-Technology Company.

Media Involved in the Following Examples are as Follows

MRS solid medium (g/L): Peptone 10 g/L, beef extract 10 g/L, glucose 20 g/L, sodium acetate 2 g/L, yeast powder 5 g/L, diammonium hydrogen citrate 2 g/L, $K_2PO_4·3H_2O$ 2.6 g/L, $MgSO_4·7H_2O$ 0.1 g/L, $MnSO_4$ 0.05 g/L, Tween 80 1 mL/L, and agar 20 g/L.

MRS liquid medium (g/L): Peptone 10 g/L, beef extract 10 g/L, glucose 20 g/L, sodium acetate 2 g/L, yeast powder 5 g/L, diammonium hydrogen citrate 2 g/L, $K_2PO_4·3H_2O$ 2.6 g/L, $MgSO_4·7H_2O$ 0.1 g/L, $MnSO_4$ 0.05 g/L, and Tween 80 1 mL/L.

Detection Methods Involved in the Following Examples are as Follows

Detection method of live count: National standard "GB 4789.35-2016 National Food Safety Standard, Food Microbiology Detection, Lactic Acid Bacteria Detection".

A Preparation Method of *Helicobacter pylori* Cells Involved in the Following Examples is as Follows:

*Helicobacter pylori* is streaked on a Columbia blood agar medium, and cultured in a three-gas incubator (85% $N_2$, 10% $CO_2$ and 5% $O_2$) at 37° C. for 3 days to obtain a single colony. The single colony is picked and inoculated in BHI medium containing 5% (v/v) fetal calf serum, and cultured in a three-gas incubator (85% $N_2$, 10% $CO_2$ and 5% $O_2$) at 37° C. for 4 days to obtain a seed solution. The seed solution is inoculated in BHI liquid medium at an inoculation amount of 2% (v/v), and the seed solution is cultured in a three-gas incubator (85% $N_2$, 10% $CO_2$ and 5% $O_2$) at 37° C. for 4 days to obtain a *Helicobacter pylori* bacterial solution. The *Helicobacter pylori* bacterial solution is centrifuged at 8,000 g for 10 min and filtered to obtain *Helicobacter pylori* bacterial cells.

The Columbia blood agar medium is prepared as follows: 39 g of Columbia medium solid powder is dissolved in 1 L of water. The solution is sterilized at 121° C. for 15 min. After cooling to 55° C. to 60° C., 7.5% (v/v) sterile defibered sheep blood is added, and the solution is mixed uniformly and poured into a plate.

A Preparation Method of *Lactobacillus rhamnosus* Cells Involved in the Following Examples is as Follows:

*Lactobacillus rhamnosus* is streaked on an MRS solid medium and cultured at 37° C. for 48 h to obtain a single colony. The single colony is picked and inoculated in MRS liquid medium, and cultured at 37° C. for 18 h for activation, and activated for two consecutive generations to obtain an activation solution. The activation solution is inoculated in MRS liquid medium at an inoculation amount of 2% (v/v) and cultured at 37° C. for 18 h to obtain a bacterial solution. The bacterial solution is centrifuged at 8,000 g for 10 min and filtered to obtain *Lactobacillus rhamnosus* bacterial cells.

Example 1: Screening and Identification of *Lactobacillus rhamnosus*

1. Screening

Fresh feces of healthy humans from Kunshan, Jiangsu was taken as a sample. The sample was pretreated, and the pretreated sample was stored in a refrigerator at −80° C. in about 30% glycerol. After the sample was taken out and thawed, the sample was mixed uniformly. 0.5 mL of the sample was pipetted and added to 4.5 mL of 0.9% physiological saline and subjected to gradient dilution. An appropriate gradient dilution was selected and spread on an MRS solid medium. The dilution was cultured at 37° C. for 48 h. Typical colonies were picked and streaked on an MRS plate for performing purification. A single colony was picked and transferred to an MRS liquid medium for performing enrichment to obtain the strain CCFM1119 (the original number of the strain is JS-SZ-2-1), and the strain was preserved with 30% glycerol in a tube.

2. Identification

The genome of the CCFM1119 was extracted, and the 16S rDNA of the CCFM1119 was amplified and sequenced (completed by Sangon Biotech (Shanghai) Co., Ltd.). By sequencing analysis, the 16S rDNA sequence of the strain is shown in SEQ ID NO. 1. The sequence was compared in GenBank, and the result showed that the strain was *Lactobacillus rhamnosus*, named *Lactobacillus rhamnosus* CCFM1119.

Example 2: Inhibition Effect of *Lactobacillus rhamnosus* on *Helicobacter pylori* Growth An MRS liquid medium was used as a negative control. *Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in MRS liquid medium at an inoculation amount of 2% (v/v), and the activation solution was cultured at 37° C. for 18 h to obtain a bacterial solution. The bacterial solution was centrifuged at 8,000 g for 10 min and filtered with a 0.22 μm sterile filter membrane to obtain supernatant. The diameter of the inhibition zone of the supernatant of *Lactobacillus rhamnosus* CCFM1119 on *Helicobacter pylori* was measured by the Oxford cup method to indicate the effect of inhibiting the growth of *Helicobacter pylori*. The measurement results are shown in Table 1. (For details of the Oxford cup method, please refer to the literature: Zhang Tingting, Zhai Qixiao, Jin Xing, et. al. Screening and characterization of lactic acid bacteria with antagonistic activities against *Campylobacter* jejuni from chicken manure. Microbiology China, 2017, (44): 118-125).

It can be seen from Table 1 that the MRS liquid medium has no inhibition zone on *Helicobacter pylori*, while the diameter of the inhibition zone of the *Lactobacillus rhamnosus* CCFM1119 supernatant on *Helicobacter pylori* can reach 12.92 mm, indicating that the *Lactobacillus rhamnosus* CCFM1119 can inhibit the growth of *Helicobacter pylori*.

TABLE 1

The diameter of the inhibition zone of *Lactobacillus rhamnosus* CCFM1119 on *Helicobacter pylori*

| Group | pH | Diametere of inhibition zone (mm) |
|---|---|---|
| Negative control | 6.20 | 0 |
| CCFM1119 | 3.54 | 12.92 ± 0.19 |

Example 3: Effect of *Lactobacillus rhamnosus* on Adhesion of *Helicobacter pylori*

Specific Steps are as Follows:
(1) Preparation of Resuspension

*Helicobacter pylori* cells were resuspended in an F12 medium to a concentration of $1 \times 10^7$ CFU/mL to obtain a *Helicobacter pylori* resuspension. *Lactobacillus rhamnosus* L. GG cells were resuspended in an F12 medium to a concentration of $1 \times 10^7$ CFU/mL to obtain a *Lactobacillus rhamnosus* L. GG resuspension. *Lactobacillus rhamnosus* CCFM1119 cells were resuspended in an F12 medium to a concentration of $1 \times 10^7$ CFU/mL to obtain a *Lactobacillus rhamnosus* CCFM1119 resuspension.

(2) Preparation of *Helicobacter pylori*-Infected AGS Cells

AGS cells were resuspended in an F12 medium containing 5% (v/v) fetal calf serum, then added to a 96-well plate ($2 \times 10^4$ cells/well), and cultured at 37° C. in 5% $CO_2$ for 12-16 h. Until the AGS cells were in an adherent state, the AGS cells were washed 3 times with PBS to remove dead cells. The *Helicobacter pylori* resuspension was added to the washed AGS cells, and cultured in an incubator at 37° C. in 5% $CO_2$ for 2 h. The AGS cells were washed with a PBS solution 3 times to remove unabsorbed *Helicobacter pylori* and obtain *Helicobacter pylori*-infected AGS cells.

(3) AGS cells not infected with *Helicobacter pylori* and not treated with *Lactobacillus rhamnosus* L. GG or *Lactobacillus rhamnosus* CCFM1119 were a blank group.

*Helicobacter pylori*-infected AGS cells not treated with *Lactobacillus rhamnosus* L. GG or *Lactobacillus rhamnosus* CCFM1119 were a model group (Hp group).

*Helicobacter pylori*-infected AGS cells treated with *Lactobacillus rhamnosus* L. GG and *Helicobacter pylori*-infected AGS cells treated with *Lactobacillus rhamnosus* CCFM1119 were experimental groups, named an Hp+LGG group and an Hp+CCFM1119 group respectively.

0.2 mL of *Lactobacillus rhamnosus* L. GG resuspension or *Lactobacillus rhamnosus* CCFM1119 resuspension was added to *Helicobacter pylori*-infected AGS cells respectively, and the cells were cultured in an incubator at 37° C. in 5% $CO_2$ for 2 h to obtain *Helicobacter pylori*-infected AGS cells treated with the *Lactobacillus rhamnosus* L. GG and *Helicobacter pylori*-infected AGS cells treated with the *Lactobacillus rhamnosus* CCFM1119. After the *Helicobacter pylori*-infected AGS cells treated with the *Lactobacillus rhamnosus* L. GG and the *Helicobacter pylori*-infected AGS cells treated with the *Lactobacillus rhamnosus* CCFM1119 were washed with a PBS solution 5 times, 200 μL of urease reagent (9 g/L NaCl, 14 μg/mL phenol red, 20 mM urea, pH 6.8) was added to the *Helicobacter pylori*-infected AGS cells treated with the *Lactobacillus rhamnosus* L. GG and the *Helicobacter pylori*-infected AGS cells treated with the *Lactobacillus rhamnosus* CCFM1119 respectively, and the cells were cultured in an incubator at 37° C. in 5% $CO_2$ for 2 h to obtain culture solutions.

The absorbance of the culture solutions of different groups was measured at a wavelength of 550 nm by using a microplate reader. The adhesion rate determined by subtracting the absorbance of the blank group from the absorbance of the model group is 100%. The relative adhesion rate was the value obtained by the absorbance of the remaining groups minus the absorbance of the blank group versus the value of obtained by the absorbance of the model group minus the absorbance of the blank group. The measurement results are shown in FIG. 1.

It can be seen from FIG. 1 that after treatment with *Lactobacillus rhamnosus* CCFM1119, the adhesion rate of *Helicobacter pylori* to the AGS cells decreased significantly, from 100% in the model group (Hp group) to about 70%. However, *Lactobacillus rhamnosus* L. GG did not significantly reduce the adhesion rate of *Helicobacter pylori* to the AGS cells, and the adhesion rate of *Helicobacter pylori* hardly changed. The result shows that *Lactobacillus rhamnosus* CCFM1119 can effectively reduce the adhesion of *Helicobacter pylori* to the AGS cells.

Example 4: Effect of *Lactobacillus rhamnosus* on Gastrointestinal Symptoms in *Helicobacter pylori*-Positive Patients

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

26 *Helicobacter pylori*-positive infected patients (Table 2 shows the population distribution of recruited patients, and the difference in baseline conditions between the two groups of people is of no statistical significance) were recruited. The 26 *Helicobacter pylori*-positive infected patients were randomly divided into 2 groups, including 13 in a placebo group (Placebo) and 13 in a *Lactobacillus rhamnosus* CCFM1119 group (CCFM1119).

The placebo group (Placebo) took placebo twice a day, and the *Lactobacillus rhamnosus* CCFM1119 group took the bacterial powder twice a day. The whole experiment period is 1 month (the placebo and the *Lactobacillus rhamnosus* bacterial powder contain different components, but the appearances and packaging of the products are the same without significant difference). The two groups of patients filled out the Gastrointestinal Symptom Rating Scale (GSRS) before and after the experiment (Table 3 shows the Gastrointestinal Symptom Rating Scale). The average value of each group was calculated to characterize the gastrointestinal health status of each group, and the improvement of gastrointestinal symptoms of patients after the experiment was evaluated. The measurement results are shown in FIG. 2.

Figure 2:
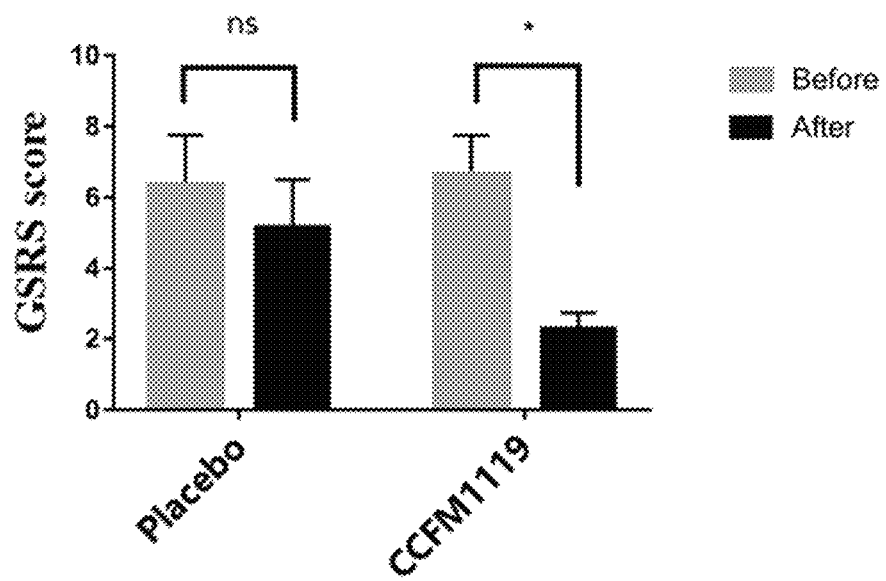
FIG. 2 shows changes in GSRS scores of Helicobacter pylori-positive patients in different groups.

It can be seen from FIG. 2 that before and after the experiment, the *Helicobacter pylori*-positive infected patients in the placebo group (Placebo) had a GSRS score 5 or above. However, the *Helicobacter pylori*-positive infected patients in the *Lactobacillus rhamnosus* CCFM1119 group (CCFM1119) had a GSRS score of about 6 before the start of the experiment, and dropped to about 2 after the end of the experiment. The result shows that *Lactobacillus rhamnosus* CCFM1119 can significantly relieve the gastrointestinal symptoms of *Helicobacter pylori*-infected patients.

TABLE 2

Population distribution of recruited *Helicobacter pylori*-positive infected patients

| Group | Number of people (N) | Age | Male/female | Drinker/non-drinker | Smoker/non-smoker |
|---|---|---|---|---|---|
| Placebo | 13 | 48.15 ± 3.70 | 2/11 | 1/12 | 0/13 |
| CCFM1119 | 13 | 51.67 ± 4.26 | 4/9 | 2/11 | 0/13 |

TABLE 3

Gastrointestinal Symptom Rating Scale

| Item | Manifestations | Score |
|---|---|---|
| Abdominal pain (Physical discomfort, subjective feeling of pain. The type of pain can be based on the patient's description and the nature of the pain. For example, upper abdominal pain, according to its typical location, can be considered as an acid-related symptom, just like the characteristics of eating and antacid relief. Hernia pain is usually severe and is located in the lower abdomen. Persistent dull pain usually lasts for a few hours and is of moderate severity. Graded according to the degree, frequency, duration, relieving factors and social activity impacts.) | No or transient pain | 0 point |
| | Occasional pain, affecting some social activities | 1 point |
| | Prolonged pain, requiring treatment, and affecting many social activities | 2 points |
| | Severe pain, affecting all social activities | 3 points |
| Heartburn (Manifested as discomfort or burning sensation behind the breastbone. Graded according to the degree, frequency, duration, relieving factors and social activity impacts.) | No or transient heartburn | 0 point |
| | Occasional short-time heartburn | 1 point |
| | Frequent and prolonged discomfort, requiring treatment to relieve | 2 points |
| | Persistent discomfort, which can only be temporarily relieved by antacids | 3 points |
| Acid reflux (Manifested as a sudden occurrence of acid reflux. Graded according to the degree, frequency, duration, relieving factors and social activity impacts.) | No or short reflux | 0 point |
| | Occasional offensive reflux | 1 point |
| | Reflux once or twice a day, requiring treatment to relieve | 2 points |
| | Reflux several times a day, antacid treatment for which can only provide short-time and insignificant relief | 3 points |
| Upper abdomen tightness (Manifested as upper abdomen tightness that can be relieved by eating or antacids. Without eating or taking medicine, the tightness sensation progresses to pain. Graded according to the degree, frequency, duration, relieving factors and social activity impacts.) | No or transient tightness sensation | 0 point |
| | Occasional short-time discomfort, requiring no food or antacids between meals | 1 point |
| | Discomfort with prolonged time and increased frequency, requiring food or antacids between meals to relieve | 2 points |
| | Persistent discomfort, frequently requiring for food or antacids | 3 points |
| Nausea and vomiting (Representing nausea and vomiting worsened by nausea. Graded according to the degree, frequency, duration, relieving factors and social activity impacts.) | No nausea | 0 point |
| | Occasional transient discomfort | 1 point |
| | Frequent and prolonged nausea, no vomiting | 2 points |
| | Persistent nausea, frequent vomiting | 3 points |
| Borborygmus (Manifested as a rumbling in the abdomen. Graded according to the degree, frequency, duration, relieving factors and social activity impacts.) | No or transient borborygmus | 0 point |
| | Short-time and occasional borborygmus and discomfort | 1 point |
| | Frequent and prolonged borborygmus, which can be controlled by activities without affecting social activities | 2 points |
| | Persistent borborygmus, seriously affecting social activities | 3 points |

TABLE 3-continued

Gastrointestinal Symptom Rating Scale

| Item | Manifestations | Score |
|---|---|---|
| Abdominal distension (Manifested as gas swelling in the abdomen. Graded according to the degree, frequency, duration, relieving factors and social activity impacts.) | No or transient abdominal distension | 0 point |
| | Short-time occasional abdominal distention | 1 point |
| | Frequent and long-time abdominal distension, which can be controlled by adjusting the dress | 2 points |
| | Persistent abdominal distension, seriously affecting social activities | 3 points |
| Belching (Graded according to the degree, frequency, duration, relieving factors and social activity impacts.) | No or transient belching | 0 point |
| | Occasional offensive belching | 1 point |
| | Frequent belching, affecting some social activities | 2 points |
| | Frequent belching, seriously affecting social activities | 3 points |
| Increased flatus (Graded according to the degree, frequency, duration, relieving factors and social activity impacts.) | No increase in flatus | 0 point |
| | Short-time occasional discomfort | 1 point |
| | Frequent and prolonged discomfort, affecting some social activities | 2 points |
| | Increased number of attacks, seriously affecting social activities | 3 points |
| Decreased defecation (Graded according to the degree, frequency, duration, relieving factors and social activity impacts.) | Once a day | 0 point |
| | Once every three days | 1 point |
| | Once every five days | 2 points |
| | Once every seven days or less | 3 points |
| Increased defecation (Graded according to the degree, frequency, duration, relieving factors and social activity impacts.) | Once a day | 0 point |
| | Three times a day | 1 point |
| | Five times a day | 2 points |
| | Seven times a day or more | 3 points |
| Loose stools (Graded according to the degree, frequency, duration, relieving factors and social activity impacts.) | Standard consistency | 0 point |
| | Slightly loose | 1 point |
| | Mushy | 2 points |
| | Watery | 3 points |
| Hard feces (Graded according to the degree, frequency, duration, relieving factors and social activity impacts.) | Standard consistency | 0 point |
| | Slightly hard | 1 point |
| | Hard | 2 points |
| | Hard and segmented | 3 points |
| A sense of urgency to defecate (Manifested as a sense of urgency to defecate, the feeling of inability to control defecation. Graded according to the degree, frequency, duration, relieving factors and social activity impacts.) | Normal control | 0 point |
| | Occasional sense of urgency to defecate | 1 point |
| | Frequent sense of urgency to defecate and the sudden need to go to the toilet, affecting social activities | 2 points |
| | Fecal incontinence | 3 points |
| Feeling of incomplete defecation | No feeling of incomplete defecation and effortless defecation | 0 point |
| | Occasional difficulty in defecation; occasional feeling of incomplete defecation | 1 point |
| | Definite difficulty in defecation, usually accompanied by a feeling of incomplete defecation | 2 points |
| | Extreme difficulty in defecation; routine feeling of incomplete defecation | 3 points |

Example 5: Effect of *Lactobacillus rhamnosus* on Colonization Amount and Clearance Rate of *Helicobacter pylori* in *Helicobacter pylori*-Positive Patients

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline for 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

26 *Helicobacter pylori*-positive infected patients (Table 2 shows the population distribution of recruited patients, and the difference in baseline conditions between the two groups of people is of no statistical significance) were recruited. The 26 *Helicobacter pylori*-positive infected patients were randomly divided into 2 groups, including 13 in a placebo group (Placebo) and 13 in a *Lactobacillus rhamnosus* CCFM1119 group (CCFM1119).

The placebo group (Placebo) took placebo twice a day, and the *Lactobacillus rhamnosus* CCFM1119 group took the bacterial powder twice a day. The whole experiment period is 1 month (the placebo and the *Lactobacillus rhamnosus* bacterial powder contain different components, but the appearances and packaging of the products are the same without significant difference). The 14C-urea breath test values of the *Helicobacter pylori*-positive infected patients in the placebo group and the *Lactobacillus rhamnosus* CCFM1119 group were measured by a 14C-urea breath test reagent bag and a tester before and after the experiment respectively, to evaluate the amount of colonization and clearance rate of *Helicobacter pylori* in the patients. The measurement results are shown in FIG. 3 and Table 4.

The evaluation criterion for the amount of colonization of *Helicobacter pylori* is: The decrease in the 14C-urea breath test values of *Helicobacter pylori*-positive infected patients after the end of the experiment compared with the 14C-urea breath test values of the *Helicobacter pylori*-positive infected patients before the start of the experiment.

The evaluation criterion for the clearance rate of *Helicobacter pylori* is as follows: The threshold of the clinical 14C-urea breath test value is 100, that is, if the 14C-urea breath test value is greater than or equal to 100, the infection of *Helicobacter pylori* is positive, and if the 14C-urea breath test value is lower than 100, the infection of *Helicobacter pylori* is negative. After the end of the experiment, whether the *Helicobacter pylori*-positive infected patient becomes negative is used to evaluate the increase of the clearance rate of *Helicobacter pylori*-positive infected patients.

Figure 3:
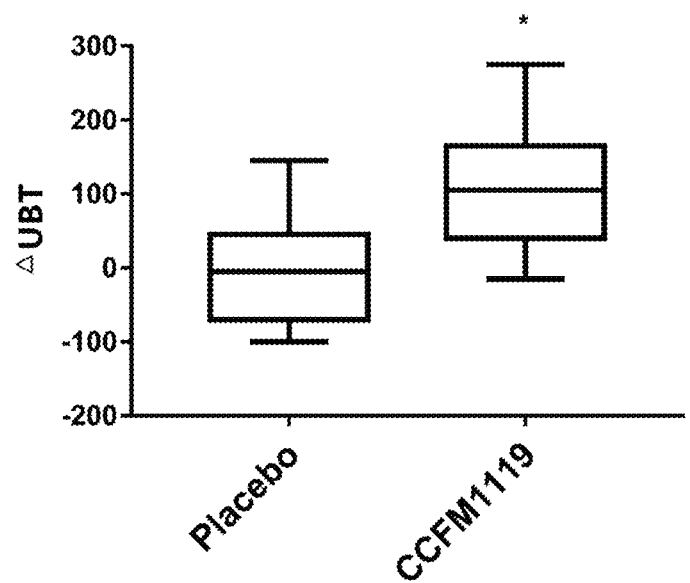
FIG. 3 shows changes in 14C-urea breath test values of Helicobacter pylori-positive patients in different groups.

It can be seen from FIG. 3 that after the end of the experiment, the 14C-urea breath test values of the *Helicobacter pylori*-positive infected patients in the placebo group (Placebo) were almost the same as before the start of the experiment. However, the 14C-urea breath test values of the *Helicobacter pylori*-positive infected patients in the *Lactobacillus rhamnosus* CCFM1119 group (CCFM1119) decreased by about 100 compared with that before the start of the experiment, and the two groups have a significant difference. The result indicates that the *Lactobacillus rhamnosus* CCFM1119 can significantly reduce the amount of colonization of *Helicobacter pylori* in *Helicobacter pylori*-infected patients.

It can be seen from Table 4 that after the end of the experiment, 2 out of 13 people in the placebo group (Placebo) became *Helicobacter pylori* negative, and the negative rate was 15.38%. Of the 13 people in the *Lactobacillus rhamnosus* CCFM1119 group, 8 people became *Helicobacter pylori* negative, and the negative rate was as high as 61.54%, which was significantly higher than that of the placebo group. The result indicates that the *Lactobacillus rhamnosus* CCFM1119 can significantly improve the clearance rate of *Helicobacter pylori* in the *Helicobacter pylori*-infected patients.

TABLE 4

Clearance rate of *Helicobacter pylori*-positive patients in different groups

| Group | Number of people (N) | Positive n | Negative n | Negative rate (%) |
|---|---|---|---|---|
| Placebo | 13 | 11 | 2 | 15.38 |
| CCFM1119 | 13 | 5 | 8 | 61.54* |

Note:
*indicates a significant difference compared with the placebo group ($p < 0.05$).

Example 6: Application of *Lactobacillus rhamnosus*

*Lactobacillus rhamnosus* CCFM1119 can be used to prepare bacterial powder. The specific preparation process of the bacterial powder is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline for 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

2 g of *Lactobacillus rhamnosus* CCFM1119 bacterial powder was accurately weighed and dissolved in 10 mL of sterile physiological saline to obtain an original bacterial suspension. 0.5 mL of the original bacterial suspension was taken and added to 4.5 mL of sterile physiological saline, and the solution was uniformly mixed. At this time, the original bacterial suspension is diluted 10 times and recorded as "n=10". 0.5 mL of the diluted bacterial suspension was taken and added to 4.5 mL of sterile physiological saline. At this time, the original bacterial suspension is diluted 100 times and recorded as "n=$10^2$". By analogy, the original bacterial suspension was diluted $1.0 \times 10^8$ times. 0.1 mL of the bacterial suspensions with dilution multiples of $1.0 \times 10^6$ (n=$10^6$), $1.0 \times 10^7$ (n=$10^7$) and $1.0 \times 10^8$ (n=$10^8$) were taken and inoculated into MRS solid medium, and put the medium upside down in an anaerobic box. The bacterial suspensions were cultured in an anaerobic box at 37° C. for 2 d to 3 d, and the live bacteria were counted. The measurement was performed once a week for one month to determine the storage stability of the *Lactobacillus rhamnosus* CCFM1119 bacterial powder. The measurement results are shown in FIG. 4.

Figure 4:
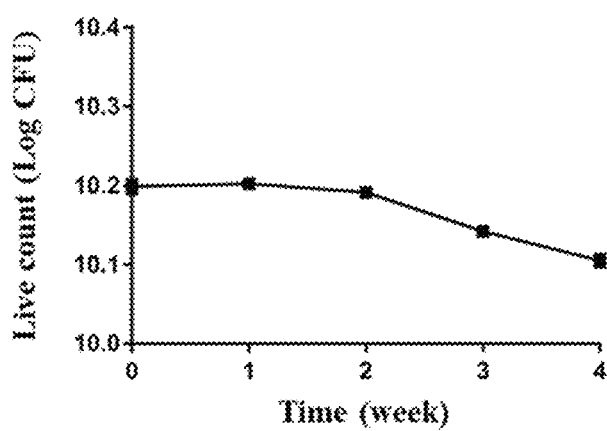
FIG. 4 shows the effect of storage time on the live count of *Lactobacillus rhamnosus* CCFM1119 bacterial powder.

It can be seen from FIG. 4 that the initial live count of the *Lactobacillus rhamnosus* CCFM1119 bacterial powder was higher than $10^{10}$ CFU/bag, and meets the product specifications. During storage for one month, the live count of the *Lactobacillus rhamnosus* CCFM1119 bacterial powder did not decrease significantly compared with the initial period, and the live count was always higher than $10^{10}$ CFU/bag, indicating that the properties of the *Lactobacillus rhamnosus* CCFM1119 bacterial powder are relatively stable during the short-term storage of one month.

Example 7: Application of *Lactobacillus rhamnosus*

*Lactobacillus rhamnosus* CCFM1119 can be used to prepare a capsule product. The specific preparation process of the capsule product is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline for 3 times and then resuspended with a protectant to a concentration of $1 \times 10^{10}$ CFU/mL to obtain a bacterial suspension. The bacterial suspension was added to a sodium alginate solution with a concentration of 30 g/L to a concentration of $2 \times 10^{9}$ CFU/mL, and then the solution was fully stirred to make the cells of *Lactobacillus rhamnosus* CCFM1119 evenly dispersed in the sodium alginate solution to obtain a mixed solution. The mixed solution was squeezed into a calcium chloride solution with a concentration of 20 g/L to form colloidal particles. After the formed colloidal particles were statically solidified for 30 min, the colloidal particles were filtered and collected. The collected colloidal particles were freeze-dried for 48 h to obtain a powder. Medicinal capsules were filled with the powder to obtain a capsule product.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

Example 8: Application of *Lactobacillus rhamnosus*

*Lactobacillus rhamnosus* CCFM1119 can be used to prepare tablets. The specific preparation process of the tablets is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

25.7 parts by weight of the *Lactobacillus rhamnosus* CCFM1119 bacterial powder, 55.0 parts by weight of starch, 4.5 parts by weight of a cellulose derivative, 12.0 parts by weight of sodium carboxymethyl starch, 0.8 parts by weight of talc, 1.0 part by weight of sucrose, and 1.0 part by weight of water were weighed to obtain raw materials. The raw materials were mixed to obtain wet granules. The wet granules were compressed using a tablet press of Zhongnan Pharmaceutical Machinery Factory, and then the tablets were dried using a small medicine dryer of Qingzhou Yikang Traditional Chinese Medicine Machinery Co., Ltd. to obtain the tablets.

Example 9: Application of *Lactobacillus rhamnosus*

*Lactobacillus rhamnosus* CCFM1119 can be used to prepare fermented milk. The specific preparation process of the fermented milk is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

The *Lactobacillus rhamnosus* CCFM1119 bacterial powder was mixed with a commercial dry powder starter *Lactobacillus bulgaricus* and a commercial dry powder starter *Streptococcus thermophilus* at a mass ratio of 1:1:1 to obtain a starter. Sugar was added to fresh milk to a concentration of 50 g/L to obtain a mixed solution. The mixed solution was homogenized at 65° C. and 20 MPa, and then heated and sterilized at 95° C. for 5 min to obtain a fermentation raw material. After the fermentation raw material was cooled to 35° C., the starer was inoculated in the fermentation raw material at an inoculation amount of 0.03% (v/v), and fermentation was performed at 35° C. for 16 h to obtain the fermented milk. After the fermented milk was stood at 42° C. for 4 h for curdling, the fermented milk was refrigerated at 4° C. for 24 h for aging to obtain the fermented milk product.

Example 10: Application of *Lactobacillus rhamnosus*

*Lactobacillus rhamnosus* CCFM1119 can be used to prepare soybean milk. The specific preparation process of the soybean milk is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1\times10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

Soybeans were soaked at a temperature of 80° C. for 2 h and then soybean hulls were removed to obtain dehulled soybeans. The dehulled soybeans were drained to remove soaking water and boiling water was added for performing pulping to obtain soybean milk. The soybean milk was kept at a temperature higher than 80° C. for 12 min to obtain cooked soybean milk. The cooked soybean milk was filtered with a 150-mesh screen and centrifugally separated to obtain crude soybean milk. The crude soybean milk was heated to a temperature of 140-150° C. and then quickly introduced into a vacuum cooling chamber and vacuumized, so that off-flavor substances in the crude soybean milk were quickly discharged with water vapor, and the cooked soybean milk was obtained. After the cooked soybean milk was cooled to about 37° C., the *Lactobacillus rhamnosus* CCFM1119 bacterial powder was added to the cooked soybean milk to a concentration of not less than $1\times10^6$ CFU/mL to obtain the soybean milk (the soybean milk needs to be stored under refrigeration at 4° C.).

Example 11: Application of *Lactobacillus rhamnosus*

*Lactobacillus rhamnosus* CCFM1119 can be used to prepare a fruit and vegetable beverage. The specific preparation process of the fruit and vegetable beverage is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1\times10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

Fresh fruits and vegetables were washed and squeezed to obtain fruit and vegetable juice. The fruit and vegetable juice was heated and sterilized at a high temperature of 140° C. for 2 seconds to obtain the sterilized fruit and vegetable juice. After the sterilized fruit and vegetable juice was cooled to about 37° C., the *Lactobacillus rhamnosus* CCFM1119 bacterial powder was added to the sterilized fruit and vegetable juice to a concentration of not less than $1\times10^6$ CFU/mL to obtain the fruit and vegetable beverage (the fruit and vegetable beverage needs to be stored under refrigeration at 4° C.).

Example 12: Application of *Lactobacillus rhamnosus*

*Lactobacillus rhamnosus* CCFM1119 can be used to prepare a milk beverage. The specific preparation process of the milk beverage is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1\times10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

The skimmed milk was heated and sterilized at 95° C. for 20 min and then cooled to 4° C. to obtain the raw material. The *Lactobacillus rhamnosus* CCFM1119 bacterial powder was added to the raw material to a concentration of not less than $1\times10^6$ CFU/mL to obtain the milk beverage (the milk beverage needs to be stored under refrigeration at 4° C.).

Example 13: Application of *Lactobacillus rhamnosus*

*Lactobacillus rhamnosus* CCFM1119 can be used to prepare chocolate. The specific preparation process of the chocolate is as follows:

*Lactobacillus rhamnosus* CCFM1119 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution is inoculated in medium at an inoculation amount of 2% (v/v), and the activation solution was cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus rhamnosus* CCFM1119 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

Cocoa mass and white granulated sugar were mixed in a mass ratio of 1:1 to 1:3, and then heated and stirred evenly to obtain a chocolate melt. First, emulsifiers (liquid lecithin, soybean phospholipid, and sorbitan monolaurate) and the *Lactobacillus rhamnosus* CCFM1119 bacterial powder were mixed uniformly in a mass ratio of emulsifiers:bacterial powder=(80-90):(10-20). Then fine grinding, acid removal, water removal, crystallization, and temperature adjustment were performed. Finally, a suitable model is selected for pouring and forming to obtain the chocolate (the chocolate needs to be stored under refrigeration at 4° C.).

Although the disclosure has been disclosed as above in preferred examples, it is not intended to limit the disclosure. Those skilled in the art can make various alterations and modifications without departing from the spirit and scope of the disclosure. Therefore, the protection scope of the disclosure should be defined by the claims.

What is claimed is:

1. A *Helicobacter pylori* inhibitor, comprising *Lactobacillus rhamnosus*,
wherein the *Helicobacter pylori* is *Helicobacter pylori* SS1;
wherein the *Lactobacillus rhamnosus* is preserved in the Guangdong Microbial Culture Collection Center, under the preservation number GDMCC NO: 61013, on May 6, 2020; and
wherein the inhibitor is a food or a medicine.

2. The *Helicobacter pylori* inhibitor according to claim 1, wherein a live count of the *Lactobacillus rhamnosus* is not less than $5 \times 10^9$ CFU/mL or $5 \times 10^9$ CFU/g.

3. The inhibitor of claim 1, wherein the inhibitor is the medicine, and wherein the medicine further comprises a drug carrier and/or a pharmaceutical excipient.

4. The inhibitor of claim 1, wherein the inhibitor is the medicine, and wherein the medicine is in a form of powders, granules, capsules, tablets, pills, or liquids.

5. The inhibitor according to claim 1, wherein the inhibitor is the food, and wherein the food further comprises dairy, bean, fruit, and/or vegetable.

\* \* \* \* \*